United States Patent [19]
Blacklock

[11] Patent Number: 5,996,453
[45] Date of Patent: *Dec. 7, 1999

[54] RATCHET MECHANISM WHICH RESISTS SPONTANEOUS DISENGAGEMENT FOR USE IN WRENCHES AND OTHER TOOLS

[75] Inventor: Gordon D. Blacklock, Albuquerque, N.Mex.

[73] Assignee: Hand Tool Design Corporation, Wilmington, Del.

[ * ] Notice: This patent is subject to a terminal disclaimer.

[21] Appl. No.: 09/009,186

[22] Filed: Jan. 20, 1998

Related U.S. Application Data

[63] Continuation-in-part of application No. 08/632,157, Apr. 15, 1996, Pat. No. 5,709,137, which is a continuation-in-part of application No. 08/427,256, Apr. 24, 1995, Pat. No. 5,653,151.

[51] Int. Cl.⁶ ..................................................... B25B 23/14
[52] U.S. Cl. ................................................. 81/467; 81/60
[58] Field of Search .............................. 81/58.5, 60, 119, 81/467

[56] References Cited

U.S. PATENT DOCUMENTS

| 161,022 | 3/1875 | Freeman. | |
|---|---|---|---|
| 3,635,654 | 1/1972 | McFarland. | |
| 4,276,791 | 7/1981 | Thompson. | |
| 5,842,391 | 12/1998 | Chaconas | 81/60 |

*Primary Examiner*—James G. Smith
*Attorney, Agent, or Firm*—Leonard Bloom

[57] ABSTRACT

A one or two sided or headed ratcheting driving wrench. Each side or head has a rotatable tool carrier constrained to rotate in only one direction by interengaging teeth formed in the tool carrier and in its housing. Both sets of teeth may be pointed or rounded. In one direction, torque locks the tool carrier to the housing, and thus drives a tool such as a screw driver blade or a socket. In the other direction, torque causes the tool carrier to disengage from the housing. Thus, intermittent one way rotation is assured. The chamber is slightly elongated, having two rows of teeth, each row separated from the other by stretches of chamber wall lacking teeth. Should the tool carrier back out of contact with one row of teeth, it will shortly engage the second row of teeth, thereby maintaining driven relationship with the working head. The wrench has a bent lever or handle to allow for working in tight quarters. The tool carrier has a square hole formed therein, for receiving a driven tool. The driven tool comprises a square block cooperating with the square hole of the tool carrier, and has two oppositely oriented blades, sockets, or other tool elements. Optionally, the square block is separate from the driven tool, and is employed with a secondary tool. Also optionally, a fastener is formed integrally with the tool carrier. The wrench preferably has provision for limiting torque acting on the driven member.

20 Claims, 9 Drawing Sheets

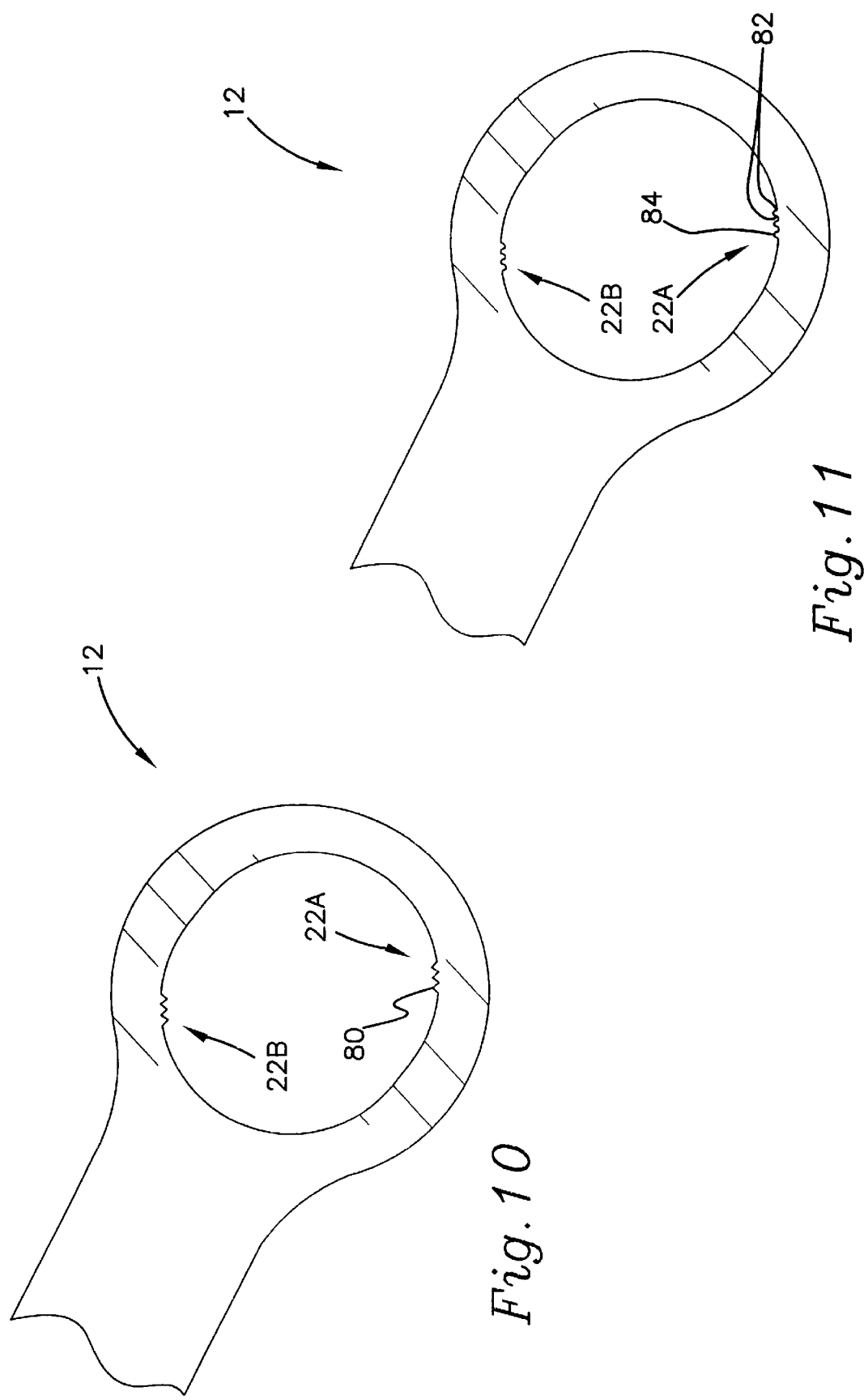

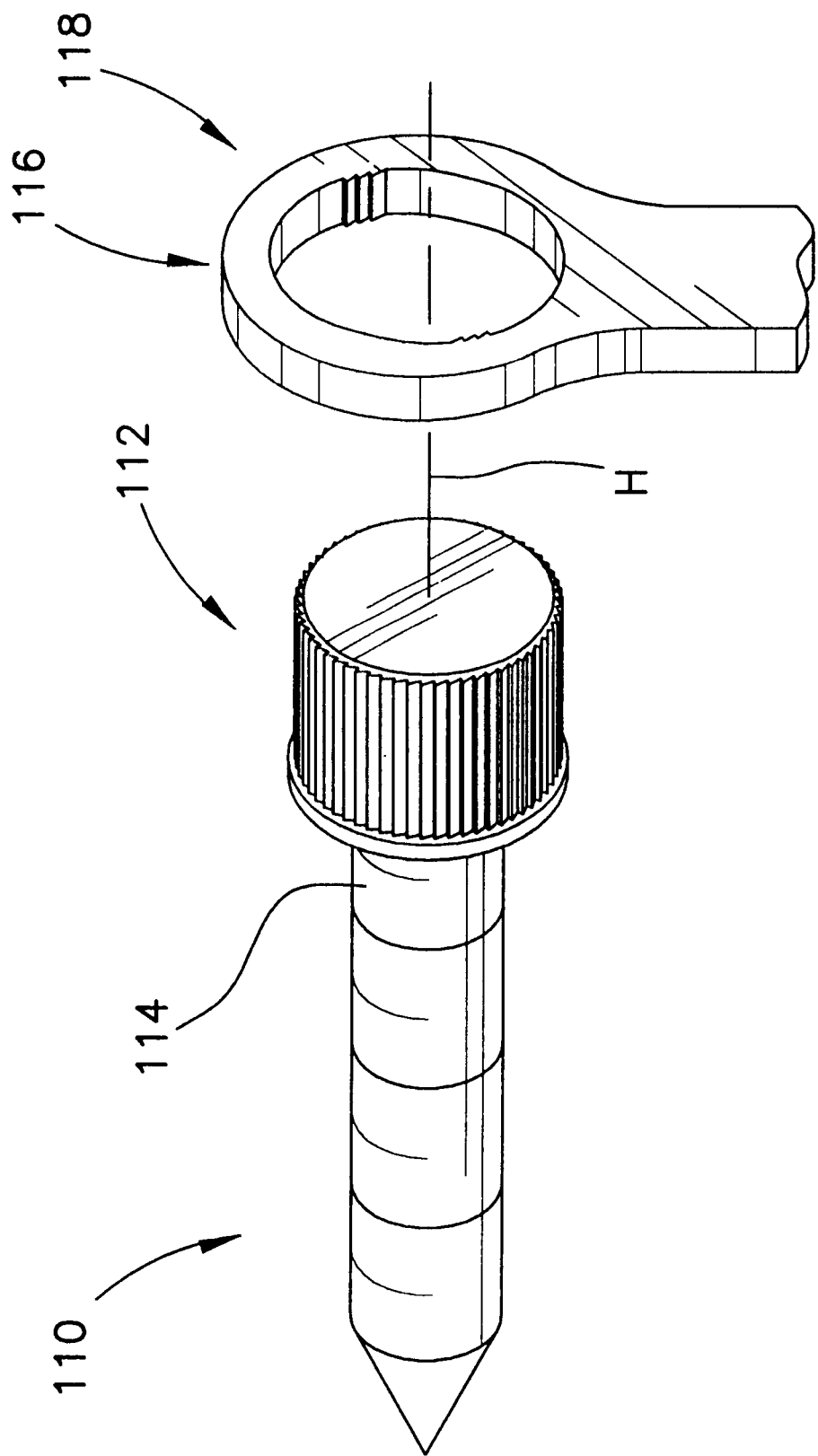

RATCHET MECHANISM WHICH RESISTS SPONTANEOUS DISENGAGEMENT FOR USE IN WRENCHES AND OTHER TOOLS

REFERENCE TO RELATED APPLICATIONS

This application is a Continuation-in-Part patent application of Ser. No. 08/632,157, filed Apr. 15, 1996, (now U.S. Pat. No. 5,709,137 issued Jan. 20, 1998) which is a Continuation-in-Part Patent Application of Ser. No. 08/427,256, which is now U.S. Pat. No. 5,653,151, issued Aug. 5, 1997.

BACKGROUND OF THE INVENTION

1. Field of the Invention

The present invention relates to a ratcheting mechanism for enabling rotation of sockets, screw driver blades, and other objects. The wrench comprises a handle giving the user leverage, and a working head which is either directly usable with square or otherwise configured drives, screw driving blades, and the like, or which may have a receptacle for interchangeably accepting various tool driving shafts.

2. Description of the Prior Art

Reversible ratcheting tools have long been desired by service and assembly mechanics and technicians for installing and removing threaded fasteners. For the convenience of the technician, it is important that a tool be quickly converted to include any desired driver, blade, socket, and so forth, since efficiency of assembly and disassembly is usually directly linked to the technician's compensation. For this reason, reversible wrenches have become quite popular.

A second desirable aspect is that a single driving tool accept interchangeable drivers, blades, sockets, fasteners, and like accessories cooperating with the driver. These drivers, blades, sockets, and like accessories will be referred to hereinafter as tools. Interchangeability enables a single wrench to perform many tasks. The wrench can gain added capabilities as additional tools are made available. This arrangement has favorable economic repercussions, since each additional size or configuration requires a working element or tool of limited complexity and cost.

An additional desirable aspect is that the wrench have as few separate parts as possible. In traditional reversible ratcheting wrench driving tools, separate internal and external parts are required to adjust the direction of operation. However, it is possible to design the wrench so as to eliminate such intermediate components. An example is seen in U.S. Pat. No. 161,022, issued to George W. Freeman on Mar. 23, 1875. The Freeman wrench has a rotatable inner member occupying a generally round cavity formed in the head thereof. The inner member has external teeth which engage a single internal tooth formed in the cavity of the head of the wrench. Both internal and external teeth have one side oriented at a severe angle to a line tangential with the respective rounded shape of the inner member or of the round cavity of the head of the wrench, the other side oriented at a slight angle to the tangential line. This arrangement is typical of pawl and ratchet devices.

However, the internal geometry and structure of this wrench differ from those of the present invention, and the differences, although some aspects being so slight as not to be readily discernible upon casual inspection, lead to significantly different performance characteristics.

Careful examination of the Freeman wrench will reveal that the internal rotatable member is not surroundably constrained in the manner of the present invention. It is possible that the rotatable member in Freeman's device will rotate out of an engaged position with respect to the fixed encircling member of the tool after only a very limited degree of rotation in response to resistance to torque applied to the wrench. In the present invention, the encircling member is dimensioned and configured to avoid this occurrence.

A number of other prior art wrenches providing reversibility and plural driving features will be reviewed. A wrench having a removable socket is shown in U.S. Pat. No. 4,276,791, issued to John W. Thompson on Jul. 7, 1981. The wrench includes the usual bipositionable pawl, and has a lever and linkage for adjusting the driving direction. The present invention is unencumbered by such a pawl and linkage.

U.S. Pat. No. 4,807,500, issued to Harvey M. Main, on Feb. 28, 1989, illustrates a ratcheting tool wherein a circular internal member has teeth disposed along only a portion of its circumference. In the present invention, it is the surrounding member that has teeth disposed on the generally circular surface of the cavity formed therein, these teeth being arranged in two diametrically opposed groups. Also, the complex, multi-part construction of the internal member of Main is replaced by a single part corresponding member in the present invention. Configuration of the cavity of the present invention is carefully varied from circular to achieve new results not seen in Main.

U.S. Pat. No. 1,359,325, issued to William A. Butler on Nov. 16, 1920, describes a ratchet wrench having a driven member disposed in an elongated slot, the driven member being able to move in the slot. Butler lacks cavity geometry and an arrangement of driving teeth disposed in two diametrically opposed groups on the internal surface of the cavity, both of these features being found in the present invention.

Italian Patent No. 603807, issued to Orlando Contini on Apr. 13, 1960, shows a ratcheting tool having tooth contact occurring along a limited length of the circumference of the circular driven member. However, the subject tool is not surrounded and constrained in the manner of the present invention.

None of the above inventions and patents, taken either singly or in combination, is seen to describe the instant invention as claimed.

SUMMARY OF THE INVENTION

The present inventive wrench combines the advantages of uncomplicated construction with the features of reversibility and interchangeability of tool varieties. The wrench has an elongated handle, and a head at each end of the handle, for containing operative components.

Each head has a member which rotates unidirectionally by a ratchet. An inner member, or tool carrier, is rotatably disposed within the head. The tool carrier is rotated with ratchet action by the following arrangement. The head has an internal chamber of generally circular configuration. Part of the circular inner wall of the head is smooth, and part has inwardly oriented teeth. The inwardly oriented teeth are arranged in two separated rows or sections, each row generally being diametrically opposed on the inner wall with respect to the other row of teeth.

This characteristic defeats spontaneous disengagement of the tool carrier from driving contact with the head when rotating the head in the driving or tightening direction. Although rotation of the head may from time to time tend to cause the tool carrier to withdraw from engagement with one row of teeth formed in the head, dimensions and configuration of the head assure that more than very limited travel by the tool carrier will result in engagement with the other row of teeth formed at the opposite end of the chamber formed in the head. Thus driving contact is almost immediately re-established.

The tool carrier has a generally circular, although toothed, external wall corresponding to the internal wall of the head. The teeth are pitched in well known fashion to interengage tool carrier and head when torque is applied in one direction, and to slip when torque is applied in the opposite direction.

The novel wrench eliminates the need for actuating levers and internal parts conventionally required to achieve ratcheting action and operation in a reverse direction by virtue of its unique geometry. Rather than being truly circular, the internal chamber of the head is very slightly elongated. The inwardly facing teeth disposed on the walls of the chamber are located such that the tool carrier occupying the chamber is prevented from rolling or migrating out of engagement with the teeth of the chamber wall when torque is applied in one direction. However, slippage occurs readily when torque is applied in the other direction. Thus, the novel wrench is clutched by torque applied to the driven device.

The tool carrier has a square hole for receiving insertable tools incorporating cooperating drivers, such as a screw driver blade, sockets, and the like, and square or other drivers not incorporating tools. A plurality of insertable tools of different dimensional and configurational characteristics gives widely diverse interchangeability of purpose.

Reversibility requires that the driver or insertable tool be removed from one face of the head of wrench, and reinstalled in the opposite face. Although it would be possible to have a driver or tool project outwardly from both faces of the head of the wrench, projection from both faces is preferably avoided in order to maintain as low a profile as possible, for working in tight quarters.

The square hole may also drive a square headed fastener directly. In such an embodiment, the wrench either lacks a square or equivalent driver. Alternatively, a fastener may be provided which incorporates characteristics of the internal, rotatable tool carrier of the wrench. In this embodiment, the wrench lacks a permanently retained tool carrier.

Reversing is accomplished by inverting the wrench within the user's hand, so that the formerly idle face of the head of the wrench, which previously faced away from the work, now faces the work. A tool or driver is now removed from one face of the head, and is reinserted into the tool carrier so that it again faces the work. However, having reversed the tool, the direction in which the tool carrier slips and locks up is changed. Effort of switching hand position of the tool is approximately the same as engaging and moving an actuating lever by finger, as is commonly performed in prior art tools to change direction.

Some other practical novel aspects of the wrench include bending of the lever or handle. In some applications, notably in the dental field, this configuration allows a dentist to work in close quarters in a person's mouth when turning a threaded component of an implant prosthesis. The wrench is two headed so that forward and reverse operation are enabled in both a right handed mode and in a left handed mode. This is again a useful feature in the dental arts, wherein a dentist may be required to perform work on both right and left sides of a patient's mouth in cramped quarters.

In an alternative embodiment, the wrench has a torque limiting feature. The portion of the chamber wall bearing internally directed teeth is formed on a cantilever spring arm or other resiliently deflectable member. When torque exceeds a predetermined value, this arm yields and moves away from the tool carrier. The tool carrier then disengages from the teeth of the chamber wall, and is no longer subject to torque.

Accordingly, it is a principal object of the invention to provide a reversing, ratchet action driving tool for driving tools such as screw driver blades and sockets.

It is another object of the invention to allow for interchangeability of individual tool sizes and types.

It is a further object of the invention to eliminate complicated internal construction of the driver.

Yet another object of the invention is to limit the amount of torque which may be applied to a tool installed in the wrench.

It is an additional object of the invention to eliminate the requirement for a separate socket for at least one size of fastener head.

It is an object of the invention to provide the wrench with offset to enable operating in tight quarters.

It is an object of the invention to maintain the back of the working head flush regardless of which direction of rotation is operative.

A further object of the invention is to provide matched pairs of wrench and fastener.

Still another object of the invention is to provide, selectively, pointed and rounded teeth.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIGS. 10 and 11 are partial top plan views of alternative forms of teeth, with a driven tool carrier omitted from each view for clarity.

FIG. 12 is an exploded, perspective view of an embodiment of the invention wherein one component of the wrench is formed integrally with a fastener or workpiece.

Similar reference characters denote corresponding features consistently throughout the attached drawings.

DETAILED DESCRIPTION OF THE PREFERRED EMBODIMENTS

Figure 1:
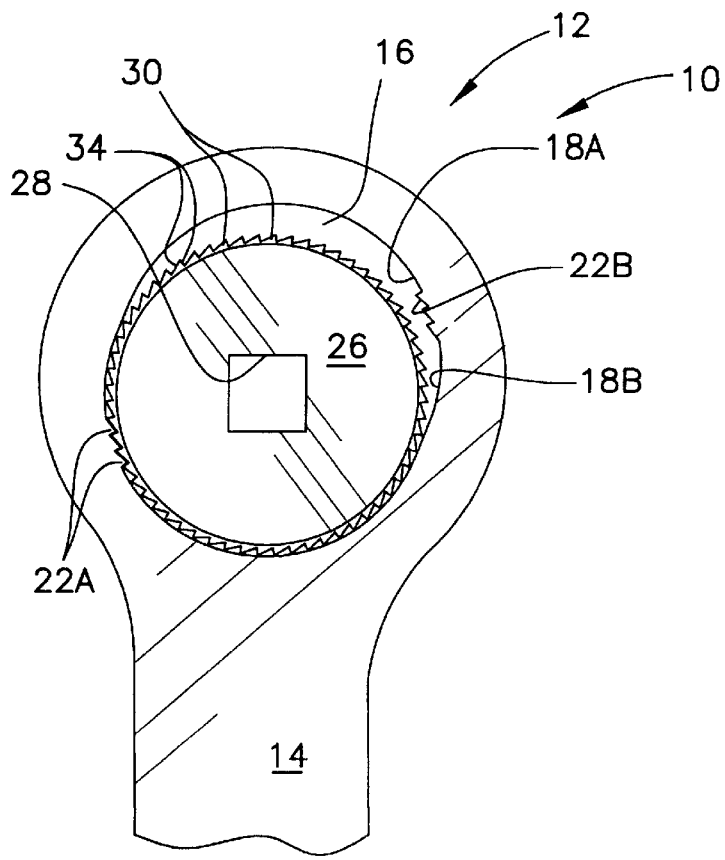
FIG. 1 is a partial top plan view of the invention.

The novel reversible ratchet mechanism or wrench 10 is seen in FIG. 1 to comprise a working head 12 having an externally projecting handle 14. Head 12 defines therein a chamber 16 having a curved internal bounding surface. Handle 14 both provides ready grasp of wrench 10, and also enables leverage for applying a torque when tightening and loosening a driven element such as a tool (illustratively, such as tool 50 of FIG. 12). Handle 14 is shown truncated, and may be of any length and configuration suitable for the intended application.

For purposes of this discussion, the ultimate driven elements will be referred to as tools. Tools will be understood to encompass any device which is insertable into or similarly engageable with the basic reversible ratchet wrench 10, and has structure for engaging wrench 10 and also has at least one working element. A working element is a screw driver blade, socket, square drive, hexagonal drive, or any other device for engaging a fastener or workpiece for the purpose of tightening and loosening the same. Alternatively, the working element engages a further working element, such as drives and adapters for adapting drive sizes, which tightens or loosens a fastener or workpiece.

It is preferred that wrench 10 be provided with a plurality of working inserts having varying geometric characteristics. A set of tools is thereby provided which requires but one driver and interchangeable working inserts to perform many tasks.

PRINCIPLE OF OPERATION

It must be noted that upon close inspection, chamber 16 is not truly circular. The overall configuration is slightly elongated, as will be explained further. Also, the internal surface of chamber 16 comprises two rows of inwardly directed teeth 22A and 22B, and two circumferential surface sections of smooth surface 18A and 18B. Each smooth surface section 18A or 18B is adjacent to and located between both rows of teeth 22A, 22B. Each smooth surface section 18A or 18B may be referred to as a pocket.

Still referring to FIG. 1, chamber 16 partially surrounds a tool driver 26, which tool driver 26 is rotatably disposed within chamber 16. Tool driver 26 is characterized by a keyed opening 28 for receiving or engaging a tool or driver (both described hereinafter) for rotatably driving a tool. Opening 28 must be other than radially symmetrical, or round, so that the inserted tool or driver is effectively driven or rotated, and will not slip ineffectually within opening 28 when torque is imposed on tool driver 26. Of course, the tool or driver inserted into opening 28 has a complementary or cooperating keyed member which fits closely within opening 28, so that it is retained by friction.

It is contemplated that in most applications, tool driver 26 will be retained within chamber 16 by provision of front and rear walls (not shown) preventing tool driver 26 from moving axially out of engagement with the internal surface of chamber 16. Such walls may be formed integrally with working head 12, or may be formed separately from and either removably or permanently attached to working head 12.

Each externally directed tooth 30 and each internally directed tooth 22A or 22B has two exposed intersecting faces 34 disposed at a pitch causing slippage between internal and external teeth 30 and 22A or 22B when wrench 10 is rotated in one direction, and causing engagement between internal and external teeth 30 and 22A or 22B when wrench 10 is rotated in the other direction. Of course, teeth 30 and 22A or 22B are dimensioned and configured to interfittably cooperate with one another while meshing.

Figure 2:
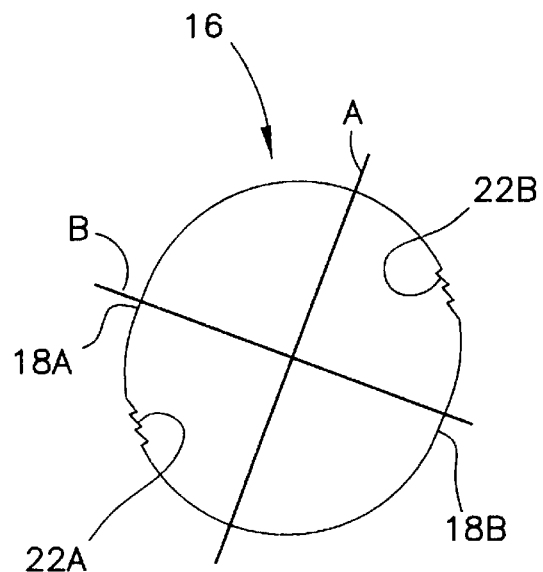
FIG. 2 is an exaggerated, diagrammatic detail view taken from FIG. 1, showing geometric relationships and characteristics of a chamber of the novel wrench.

FIG. 2 illustrates important geometry enabling wrench 10 to operate. Chamber 16, exaggerated in this view for clarity of understanding, is seen to have a major diameter A and a minor diameter B. Minor diameter B has a dimension of magnitude less than that of major diameter A. Thus, the overall configuration of chamber 16 is oval when considered in the plan view of FIG. 2. Tool driver 26 (see FIG. 1) has a diameter of magnitude slightly less than that of minor diameter B in order to fit into chamber 16.

This geometry enables engagement and disengagement of tool driver 26 responsive to a combination of applied torque and tooth pitch. When a fastener (illustratively, such as tool 50 of FIG. 12) encounters resistance, the effort of turning wrench 10 develops a torque acting on tool driver 26.

Given the relative position of teeth 22A, 22B with respect to major and minor diameters A and B, in one direction of rotation, tool driver 26 is urged into effective engagement of teeth 22A or 22B because chamber 16 lacks sufficient diameter to allow tool driver 26 to roll or migrate out of engagement. In the other direction of rotation, chamber 16 provides sufficient clearance to allow tool driver 26 to back out of engagement with teeth 22A or 22B by entering or partially occupying a pocket. The diameter of tool driver 26 is greater than minor diameter B and smaller than major diameter A, so that tool driver may move selectively into and out of engagement with working head 12 responsive to torque applied to working head 12.

As wrench 10 is alternately rotated in opposing directions, ratcheting action ensues as tool driver 26 alternately engages teeth 22A or 22B and rotates in lockstep with working head 12, and subsequently disengages teeth 22A or 22B, tool driver 26 remaining in a constant position as working head 12 is rotated in a direction opposite that rotating tool driver 26 in lockstep with working head 12.

In summary, tool driver 26 selectively engages the internal surface of chamber 16 and disengages therefrom. Tool driver 26 is constrained against disengagement by torque applied in one direction, and disengages responsive to torque applied in an opposite direction. However, disengagement while rotating in one direction, which could occur as the user's hand position varies, is limited to very short time duration since withdrawal of tool driver 26 from engagement with one row of teeth 22A or 22B will promptly result in engagement with the other teeth 22B or 22A.

FEATURES OF THE INVENTION

Figure 3:
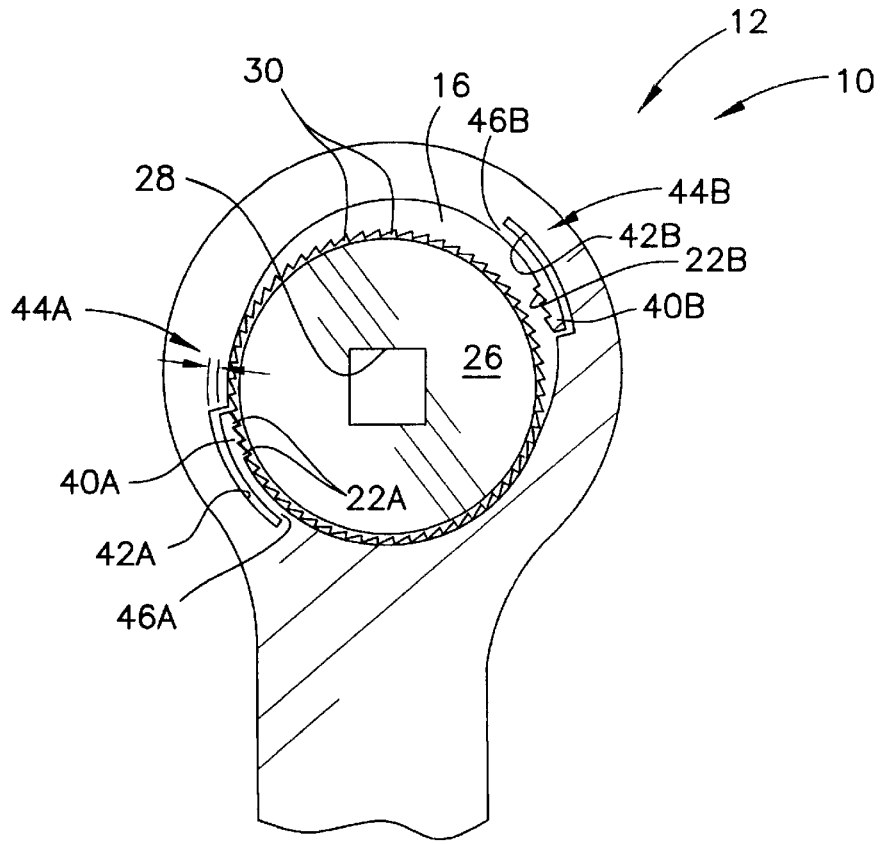
FIG. 3 is a top plan view of an alternative embodiment of the invention incorporating a feature limiting maximum torque which may be applied.

Turning now to FIG. 3, an optional torque limiting feature of wrench 10 is explained. In the event that a driven tool (not shown) encounters resistance during tightening that would damage wrench 10, the tool, or a fastener (not shown), it is possible to protect these items by limiting torque applied to tool driver 26. In this embodiment, teeth 22A, 22B are supported or disposed upon respective arms 40A, 40B anchored to working head 12.

Figure 4:
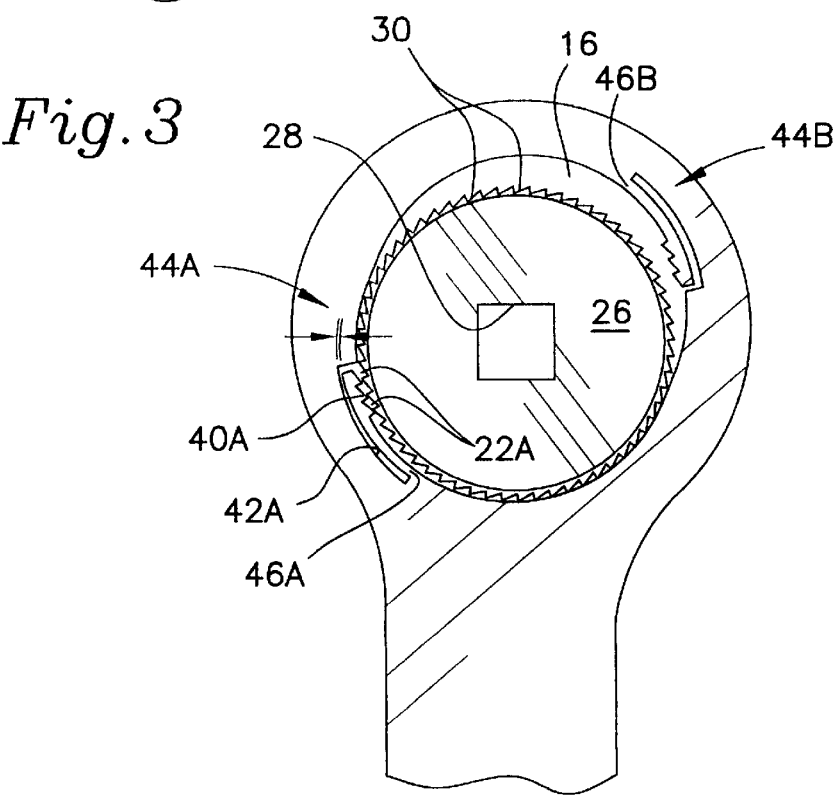
FIG. 4 is similar to FIG. 3, but illustrates deflection under excessive torque.

Each arm 40A or 40B is normally disposed at a first position, this being illustrated in FIG. 3, such that engagement of teeth 30 and teeth 22A or 22B is assured. As shown in FIG. 4, under great resistance, arm 40A or 40B deflects, withdrawing away from the center of chamber 16 into a second position. Teeth 30 and 22A or 22B thereby move out of mutual engagement. Close examination will reveal reduction of magnitude of a gap 44A or 44B in FIG. 4, as contrasted to that of FIG. 3. This arrangement limits the maximum torque which will result in driving of tool driver 26.

Spring action biasing arm 40A or 40B into the first position is provided by virtue of the nature of the material from which working head 12 is fabricated. In this embodiment, working head 12 is fabricated from a material having a known degree of elasticity or resilience. Arms 40A, 40B could be deleted in favor of any other suitable member having resilient or elastic deflection enabling teeth 22A, 22B to disengage from teeth 30 responsive to excessive torque.

Channels 42A, 42B are formed in working head 12. Channels 42A, 42B define their respective arms 40A, 40B, and determine magnitude of gap 44A or 44B separating arm 40A or 40B from surrounding working head 12. Monolithic or integral construction of working head 12 and arms 40A, 40B provides anchoring generally designated at 46A, 46B.

It is an easy matter to determine appropriate thickness of an arm 40A or 40B for predetermining appropriate force of elasticity or resiliency acting on arm 40A or 40B, based upon characteristics of the material of working head 12. This calculation and appropriate dimensioning will result in resilient deflection occurring at a predetermined amount of torque required to disengage tool driver 26 from working head 12.

Figure 5:
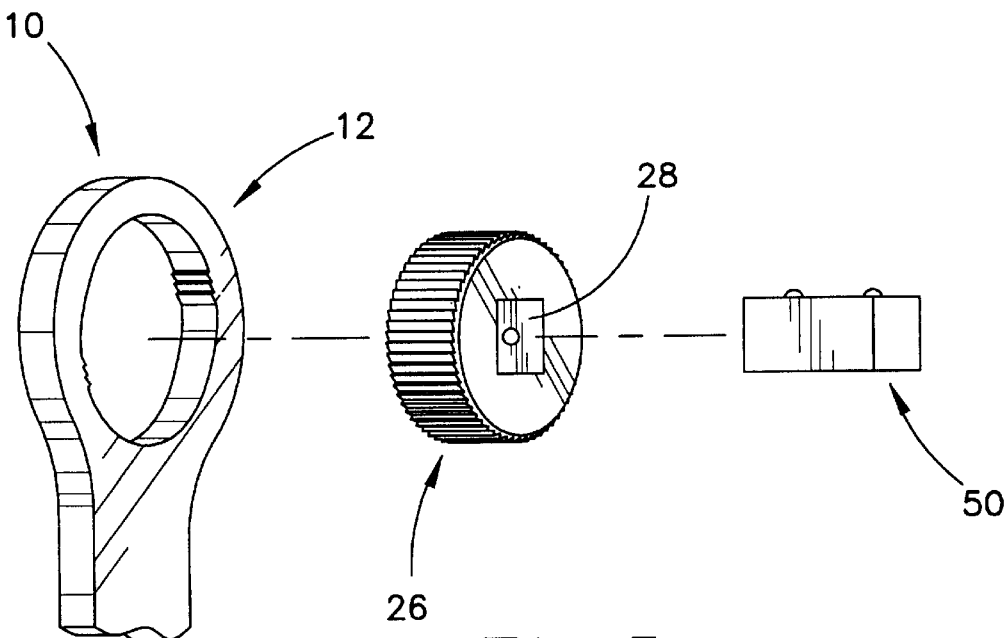
FIG. 5 is an exploded, perspective view of a feature of the invention providing a removable driving tool.

Turning now to FIG. 5, a versatile driving arrangement is shown. Tool driver 26 has opening 28 which is preferably a square hole capable of accepting insertion of a square shank of a tool (not shown). However, it is preferable to provide a driving tool 50 comprising a complementary keyed member, in this example a square member, which cooperatingly interfits within or engages opening 28.

Figures 6, 7:
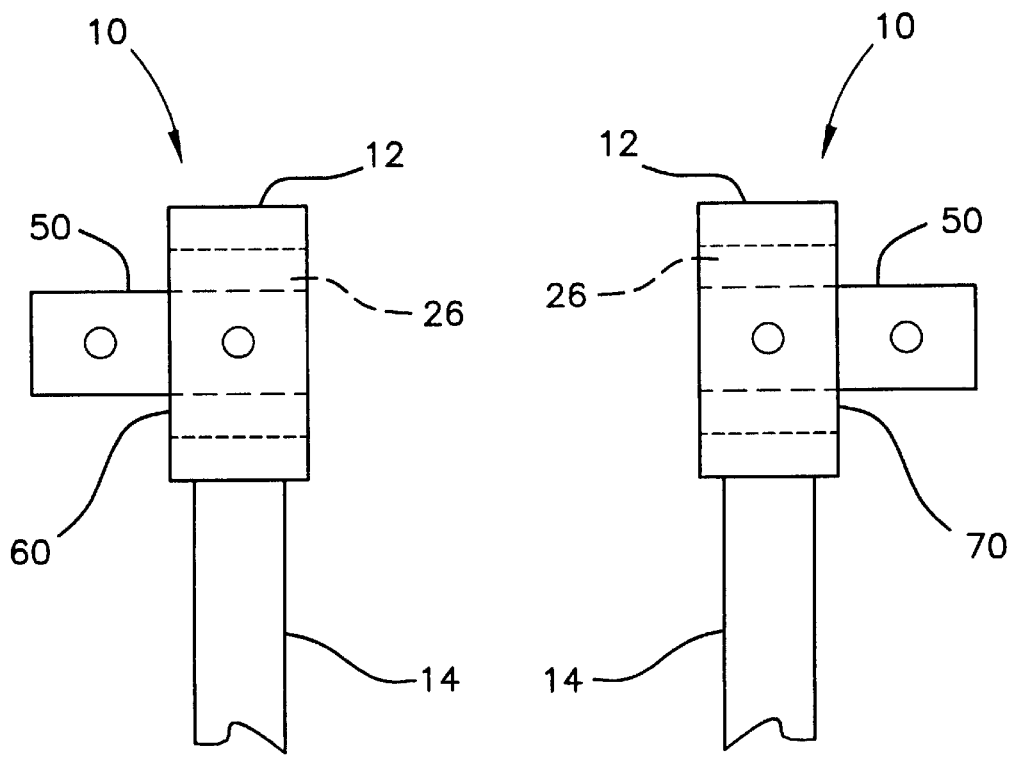
FIGS. 6 and 7 are similar side elevational views of the embodiment of FIG. 5, illustrating alternate positions of the removable driving tool.

With reference to FIG. 6, tool 50 is dimensioned and configured to project beyond tool driver 26 when installed therein. That portion of tool 50 which is exposed can in turn engage secondary tools (not shown). Secondary tools will be understood to encompass tools such as sockets, blades, and other tools having a female receptacle cooperatingly interfitting the exposed portion of tool 50.

Comparing FIGS. 6 and 7, it will be seen that tool 50 can be moved to project from both sides of working head 12. This enables both clockwise and counterclockwise rotation of a tool, while simultaneously maintaining the overall profile of wrench 10 as compact as possible. This is important since the many uses of wrench 10 include tasks which require working in tight or cramped quarters.

Figure 8:
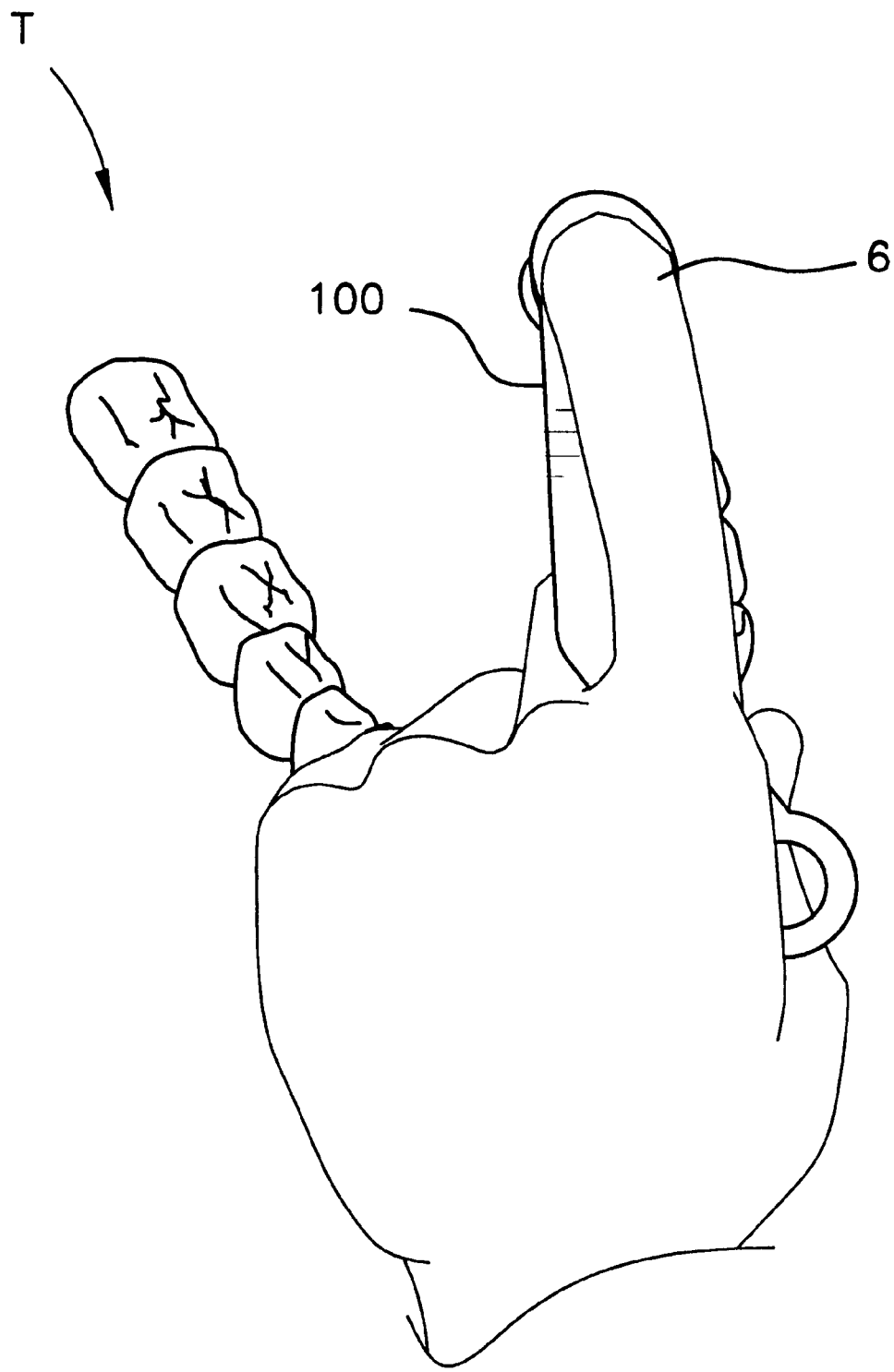
FIG. 8 is an environmental view of an embodiment of the invention, illustrating a dental application of the novel wrench.

An example of such an application is illustrated in FIG. 8. A dentist installing a dental implant or prosthesis in a patient's teeth T may possibly be required to install and remove a healing cap or other threaded component of the implant. As illustrated in this view, the dentist must work from the outside of the mouth. With index finger 6 pressing downwardly on wrench 100 to ensure engagement of the tool blade (not shown) within a cooperating socket of the implant component (not shown), possible positions of the dentist's hand are limited.

Figure 9:
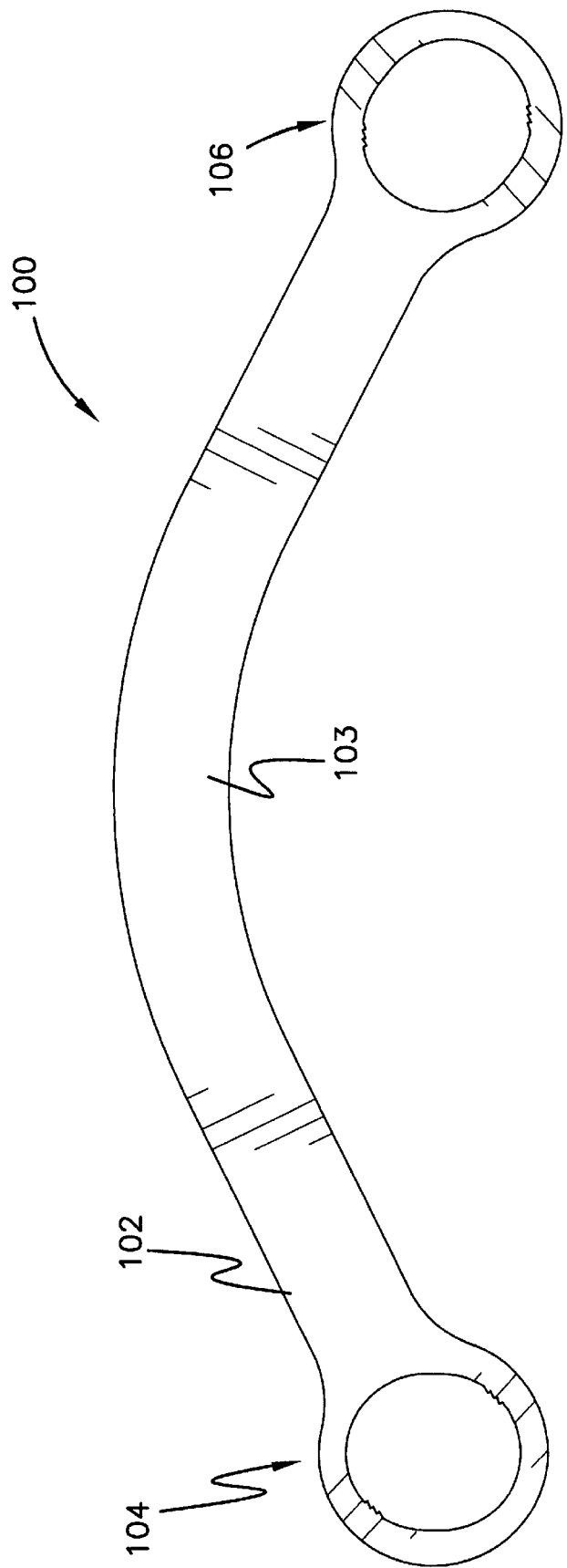
FIG. 9 is a top plan view of the embodiment of FIG. 8, with some components omitted for clarity.

As seen in FIG. 9, wrench 100 incorporating the novel features described above has a handle 102 including a bend at 103. This bend causes handle 100 accommodates the dentist's hand, as illustrated in FIG. 8.

A further feature of wrench 100 is illustrated in FIG. 9, wherein wrench 100 has two working heads 104, 106. Both working heads 104, 106 have chambers and tool drivers (omitted for clarity in this view) similar to those of the embodiment of FIG. 1. Configuration of the omitted elements are substantially similar to those shown in FIG. 1. The embodiment of FIG. 9 is particularly suited for dental work, wherein the bend at 104 enables both tightening and slackening of components to be performed in opposite hand fashion in dental work. Either head 104 or 106 may be selected, with a suitable tool (not shown) projecting from either one face 60 (see FIG. 6) or its opposed counterpart 70 (see FIG. 7). Therefore, maximal versatility and compactness are simultaneously achieved in wrench 100.

A further optional feature is described with reference to FIG. 10. It will be recalled from FIG. 1 that teeth 30 and teeth 22A, 22B are both formed to include intersecting faces 34. Throughout the drawing figures thus far described, such teeth intersect at a point, this being particularly pointed out at 80 in FIG. 10.

Alternatively, as seen in FIG. 11, faces 82 may intersect at a curved corner 84. In this instance, teeth 22A, 22B are rounded. Although teeth 30 have been omitted from FIGS. 10 and 11 for clarity, it is to be understood that they are present in the invention. It will also be appreciated that teeth 30, 22A, 22B are interchangeable since they must interfit. It is preferred that teeth 30, 22A, 22B be similar in configuration, either both being pointed, as in FIG. 10, or both rounded, as in FIG. 11.

Turning now to FIG. 12, the invention may be practiced such that a fastener 110 incorporates features of tool driver 26 of FIG. 1. In the embodiment of FIG. 12, tool driver 112, which rotates about axis H of rotation when being turned, has a threaded shank 114 projecting coaxially from tool driver 112 with respect to axis H of rotation. In this embodiment, threaded fastener 110 incorporating the improvements set forth above is readily driven by a ratchet wrench 116. A supply of fasteners 110 may be employed with wrench 116, which comprises only working head 118 and handle 120, wrench 116 lacking tool driver 26 of the embodiment of FIG. 1. This arrangement expedites installation and removal of specialized or dedicated fasteners 110, while requiring a specialized or dedicated wrench 116 which readily enables ratcheting turning of fasteners 110.

Figure 13:
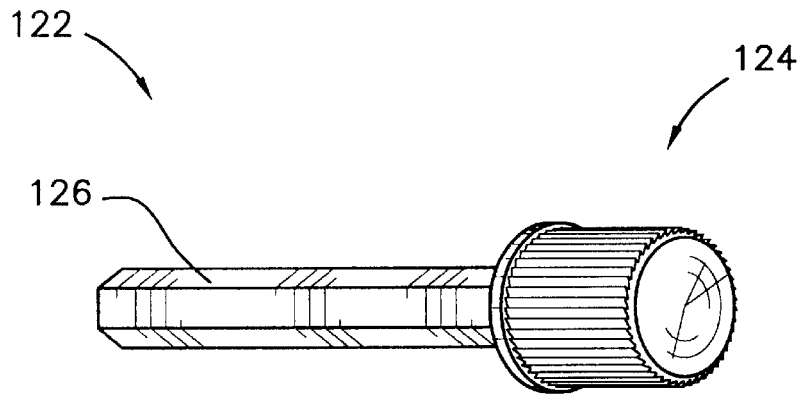
FIG. 13 is a perspective view of an alternative embodiment of the invention wherein the wrench incorporates a hexagonal driver.

FIG. 13 shows a variation of the embodiment of FIG. 12. In the embodiment of FIG. 13, tool driver 122 has a head 124 similar to that of fastener 110, enabling tool driver 122 to be rotated by wrench 116 of FIG. 12. However, shank 126 is hexagonal, so that in combination, wrench 116 and tool driver 122 may be employed to turn fasteners and work pieces (neither shown) having hexagonal holes for receiving drive tools.

In the prior embodiments, the novel ratchet mechanism comprises a working head and a relatively rotatable tool driver. The working head and tool driver form the first two components of a series of four cooperating yet separable elements. The third element of the series is a tool mounted to the tool driver, and the fourth element is a fastener or work piece driven by the tool. In the embodiment of FIG. 13, the tool driver and tool are integral, so that the series of cooperating yet separable components numbers threes the third component being the fastener or work piece.

Figure 14:
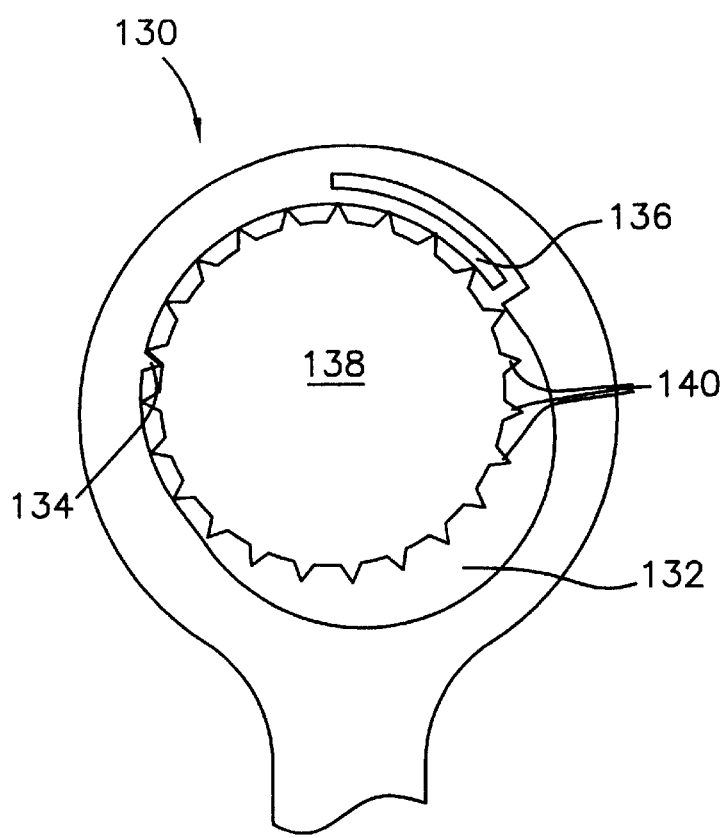
FIG. 14 is a plan view illustrating an alternative embodiment of the torque limiting feature of FIG. 3.

FIG. 14 depicts a variation on the embodiment of FIG. 3. In the embodiment of FIG. 14, working head 130 has a chamber 132, an internally directed tooth 134, and a spring arm 136. Unlike the embodiment of FIG. 3, spring arm 136 has a smooth surface devoid of teeth. Chamber 132 has a major diameter and a minor diameter in a manner similar to the prior embodiments. Tool driver 138 has externally directed teeth 140, and engages and disengages working head 130 in a manner similar to that of the prior embodiments. Spring arm 136 has a predetermined resilient yield strength such that it resiliently deflects to enable tool driver 138 to resist rotation relative to working head 130 when resistance to rotation of tool driver 138 generates force exceeding and overcoming the predetermined resilient yield strength of spring arm 136. By this manner, torque imposed upon tool driver 138 responsive to rotation of working head 130 never exceeds a predetermined maximum torque. Of course, the effect of spring arm 136 may be achieved by structure other than that of arm 136. Any resiliently deflectable member forming the internal surface of chamber 132 may be substituted for arm 136. For example, the entire body of the working head could be resiliently deflectable so as to provide the function of spring arm 136. As in prior embodiments, the overall diameter of tool driver 138 is such that it can selectively maintain and lose engagement with working head 130.

Figure 15:
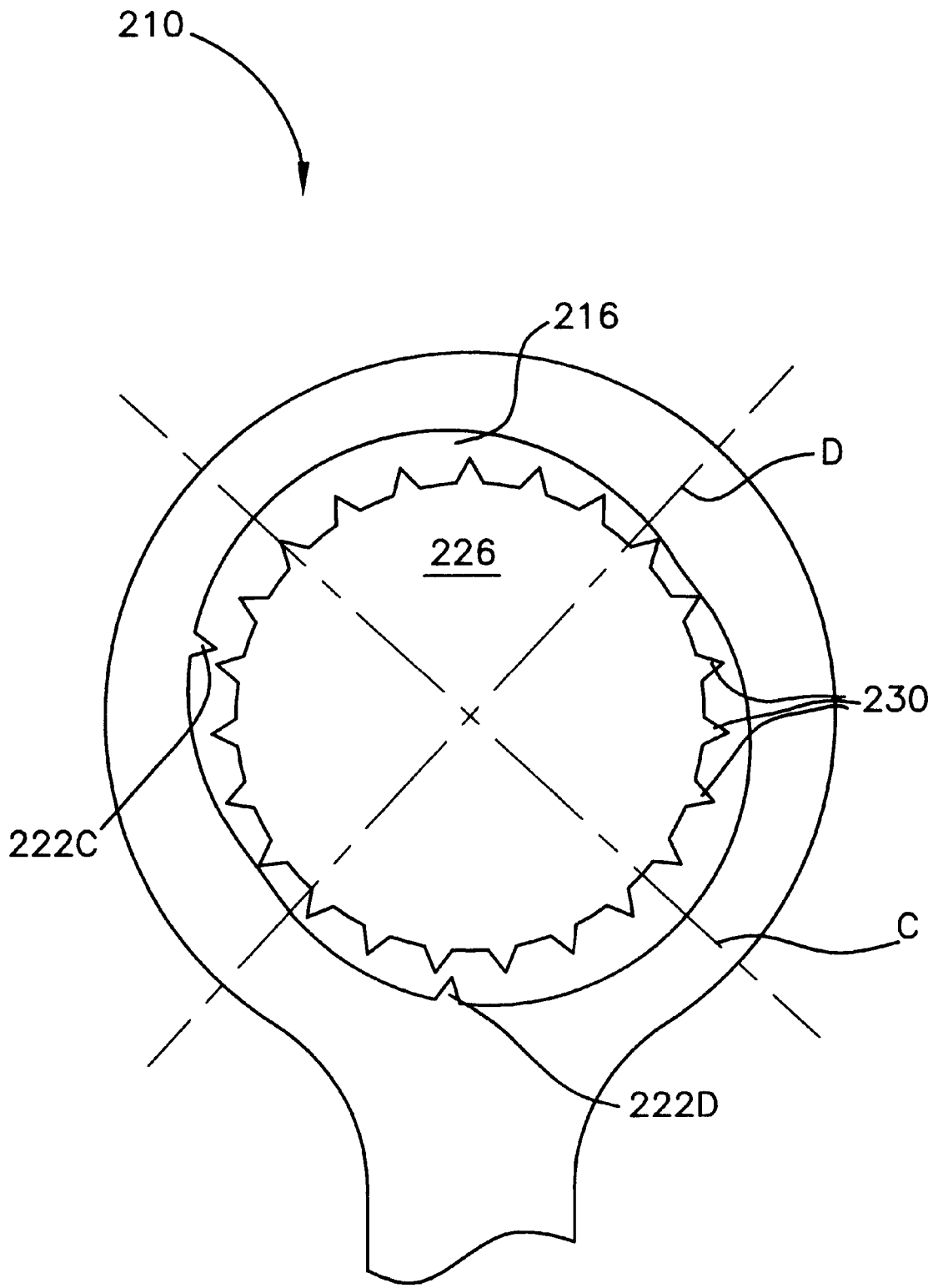
FIG. 15 is a plan view of yet another embodiment of the invention.

Referring now to FIG. 15, yet another embodiment of the invention is shown. In this embodiment the working head 210 has a chamber 216 and the tool driver is designated at 226, with its externally directed teeth indicated at 230. Chamber 216 has a major diameter C and a minor diameter D. Internally directed teeth 222C and 222D are located within chamber 216. The placement of teeth 222C and 222D allow for the wrench to be reversible without having to flip it over. If the user pushes the wrench it will ratchet in one direction and if the user pulls the device, it will ratchet in the other.

It will be apparent that many other variations and modifications to the invention are possible. For example, opening 28 of tool driver 26 may be other than square. Tools not thus far described may be employed with the novel wrench. Myriad further variations are possible.

Therefore, it is to be understood that the present invention is not limited to the embodiments described above, but encompasses any and all embodiments within the scope of the following claims.

I claim:

1. A ratchet mechanism having interchangeable working inserts, comprising:
    a working head having a handle and having means defining a chamber therein, said chamber having an internal surface having a first portion including at least one internally directed tooth and a second portion of smooth surface, a third portion including at least one internally directed tooth and a fourth portion of smooth surface, said first portion separated from said third portion by said second portion at one side of said first portion and by said fourth portion at another side of said first portion, the at least one internally directed tooth in the first portion being opposed to the at least one internally directed tooth in the third portion,
    said chamber having a major diameter and a minor diameter, said diameters designating said respective portions, and
    a tool driver rotatably disposed within said chamber, said tool driver having a circular external surface including externally directed teeth interfittably cooperating with said at least one internally directed tooth of said working head, said tool driver further having means for engaging a working insert usable with said ratchet mechanism, wherein said externally directed teeth of said tool driver may be moved into interfitting engagement of said at least one internally directed tooth of said working head when said handle is rotated in a first direction and out of engagement with said working head and said externally directed teeth of said tool driver may be moved away from interfitting engagement of said at least one internally directed tooth of said working head when said handle is rotated in a second direction opposite of said first direction.

2. The ratchet mechanism according to claim 1, said means for engaging a working insert further including an opening formed in said tool driver, for receiving a working insert insertable thereinto, and including means for preventing relative rotation of the working insert and said tool driver.

3. The ratchet mechanism according to claim 2, said opening formed in said tool driver being a square hole.

4. The ratchet mechanism according to claim 1, said resilient bias means comprising a spring normally urging said externally directed teeth of said tool driver into interfitting engagement of said internally directed teeth of said working head.

5. The ratchet mechanism according to claim 1, said means for engaging a working insert comprising an opening keyed to drivably receive fasteners.

6. The ratchet mechanism according to claim 1, said tool driver having a lateral surface and a tool projecting from said lateral surface.

7. The ratchet mechanism of claim 13, wherein the at least one internally-directed tooth in the first portion and the at least one internally-directed tooth in the third portion are each generally triangular, having two exposed intersecting faces disposed at a pitch, the externally-directed teeth on the tool driver being generally triangular to interfittingly engage the internally-directed teeth.

8. A reversible ratchet wrench for driving interchangeable tools, comprising:
    a first working head having an externally projecting handle and a chamber formed within said first working head, said chamber having a concave, curved internal surface having a first circumferential surface section including:
        a first row of internally directed teeth,
        a second, adjacent circumferential surface section of smooth surface,
        a third adjacent circumferential surface section including a second row of internally directed teeth, said second row of internally directed teeth being opposed to said first row of internally directed teeth, and
        a fourth circumferential surface section of smooth surface disposed between said first circumferential surface section and said third circumferential surface section, said internal surface having major diameter dimension and a minor diameter dimension, said major and minor diameter dimensions designating said respective sections;
    a driven tool carrier rotatably disposed within said chamber, said tool carrier having a generally circular external surface having externally directed teeth interfittably cooperating selectively with said first row and said second row of internally directed teeth of said working head, said tool carrier further having tool engaging apparatus keyed to drivably engage a tool usable with said reversible ratchet wrench,
    each one of said externally directed teeth of said tool carrier and said rows of internally directed teeth of said working head being generally triangular and having two exposed intersecting faces disposed at a pitch causing slippage when said reversible ratchet wrench is rotated in one direction and causing engagement when said reversible ratchet wrench is rotated in the other direction, said tool carrier having a tool carrier diameter dimension of magnitude slightly less than that of said minor diameter dimension of said internal surface of said chamber of said first working head, such that said externally directed teeth of said tool carrier are constrained against moving out of engagement with said selected row of internally directed teeth of said first working head when said reversible ratchet wrench is rotated against a resistance in a first direction, a torque arising from the resistance and urging said tool carrier into engagement with said working head, and said externally directed teeth of said tool carrier are enabled to move out of engagement with said selected row of internally directed teeth of said working head when said reversible ratchet wrench is rotated in an opposite direction, and contact is made between said tool carrier and said second circumferential surface section of said chamber when said externally directed teeth are disposed in driving contact with said selected row of internally directed teeth of said working head, whereby said externally directed teeth of said tool carrier engage said selected row of internally directed teeth of said internal surface of said chamber such that when said tool carrier selectively engages said internal surface of said chamber, said tool carrier is constrained against disengagement by torque applied in one direction, and said tool carrier disengages from said internal surface of said chamber responsive to torque applied in an opposite direction.

9. The reversible ratchet wrench according to claim 8, said handle having a bend therein, said bend enabling said handle to accommodate a user's hand, whereby said handle assists the user to work in cramped quarters.

10. The reversible ratchet wrench according to claim 8, further comprising a second working head and a second chamber therein, said second chamber disposed upon said handle at an end opposite that bearing said first working head and having internal cross sectional configuration substantially similar to that of said chamber of said first working head.

11. The reversible ratchet wrench according to claim 8, said two faces of each one of said externally directed teeth of said tool carrier and of each one of said internally directed teeth of said internal surface of said chamber of said first working head intersecting at a point, whereby said teeth are pointed.

12. The reversible ratchet wrench according to claim 8, said two faces of each one of said externally directed teeth of said tool carrier and of each one of said internally directed teeth of said internal surface of said chamber of said first working head intersecting at a curved corner, whereby said teeth are rounded.

13. The reversible ratchet wrench according to claim 8, said apparatus for engaging a tool being a keyed opening, whereby a tool having a complementary male keyed member is insertable into said tool carrier and is rotatably driven by said reversible ratchet wrench.

14. The reversible ratchet wrench according to claim 13, further comprising a driving tool having a complementary keyed member interfittably engaging said keyed opening of said tool carrier, said keyed member being dimensioned and configured to project beyond said tool carrier when installed therein, whereby said complementary keyed member is engageable with secondary tools.

15. A reversible ratchet wrench for driving interchangeable tools, comprising:

a first working head having an externally protecting handle and a chamber formed within said first working head, said chamber having a concave, curved internal surface having a first circumferential surface section including:

a first row of internally directed teeth, a second, adjacent circumferential surface section of smooth surface, a third adjacent circumferential surface section including a second row of internally directed teeth, and a fourth circumferential surface section of smooth surface disposed between said first circumferential surface section and said third circumferential surface section, said internal surface having a minor diameter dimension;

a driven tool carrier rotatable disposed within said chamber, said tool carrier having a generally circular external surface having externally directed teeth interfittably cooperating with said first row and said second row of internally directed teeth of said working head, said tool carrier further having tool engaging apparatus keyed to drivably engage a tool usable with said reversible ratchet wrench, each one of said externally directed teeth of said tool carrier and said rows of internally directed teeth of said working head being triangular and having two exposed intersecting faces disposed at a pitch causing slippage when said reversible ratchet wrench is rotated in one direction and causing engagement when said reversible ratchet wrench is rotated in the other direction, said tool carrier having a tool carrier diameter dimension of magnitude slightly less than that of said minor diameter dimension of said internal surface of said chamber of said first working head, such that said externally directed teeth of said tool carrier are constrained against moving out of engagement with said rows of internally directed teeth of said first working head when said reversible ratchet wrench is rotated against a resistance in a first direction, a torque arising from the resistance and urging said tool carrier into engagement with said working head, and said externally directed teeth of said tool carrier are enabled to move out of engagement with said rows of internally directed teeth of said working head when said reversible ratchet wrench is rotated in an opposite direction, and contact is made between said tool carrier and said second circumferential surface section of said chamber when said externally directed teeth are disposed in driving contact with said rows of internally directed teeth of said working head, whereby said externally directed teeth of said tool carrier engage said rows of internally directed teeth of said internal surface of said chamber such that when said tool carrier selectively engages said internal surface of said chamber, said tool carrier is constrained against disengagement by torque applied in one direction, and said tool carrier disengages from said internal surface of said chamber responsive to torque applied in an opposite direction, further including means for limiting torque applied to said tool carrier, comprising a first arm anchored to said chamber of said working head, said first arm supporting one said row of internally directed teeth of said working head, said first arm having means for moving into a first position assuring engagement of one said row of internally directed teeth of said working head with said externally directed teeth of said tool carrier and into a second position disengaging one said row of internally directed teeth of said working head from said externally directed teeth of said tool carrier, and said first arm having a first spring biasing said first arm into said first position.

16. The reversible ratchet wrench according to claim 15, said means for limiting torque applied to said tool carrier further comprising a second arm anchored to said chamber of said working head, said second arm supporting the other said row of internally directed teeth of said working head, said second arm having means for moving into a first position assuring engagement of the other said row of internally directed teeth of said working head with said externally directed teeth of said tool carrier and into a second position disengaging the other said row of internally directed teeth of said working head from said externally directed teeth of said tool carrier, said second arm having a second spring biasing said second arm into said first position.

17. A reversible ratchet wrench for driving interchangeable tools, comprising:

a first working head having an externally protecting handle and a chamber formed within said first working head, said chamber having a concave, curved internal surface having a first circumferential surface section including:
a first row of internally directed teeth,
a second, adjacent circumferential surface section of smooth surface,
a third adjacent circumferential surface section including a second row of internally directed teeth, and
a fourth circumferential surface section of smooth surface disposed between said first circumferential surface section and said third circumferential surface section, said internal surface having a minor diameter dimension;

a driven tool carrier rotatably disposed within said chamber; said tool carrier having a generally circular external surface having externally directed teeth interfittably cooperating with said first row and said second row of internally directed teeth of said working head, said tool carrier further having tool engaging apparatus keyed to drivably engage a tool usable with said reversible ratchet wrench, each one of said externally directed teeth of said tool carrier and said rows of internally directed teeth of said working head being triangular and having two exposed intersecting faces disposed at a pitch causing slippage when said reversible ratchet wrench is rotated in one direction and causing engagement when said reversible ratchet wrench is rotated in the other direction, said tool carrier having a tool carrier diameter dimension of magnitude slightly less than that of said minor diameter dimension of said internal surface of said chamber of said first working head, such that said externally directed teeth of said tool carrier are constrained against moving out of engagement with said rows of internally directed teeth of said first working head when said reversible ratchet wrench is rotated against a resistance in a first direction, a torque arising from the resistance and urging said tool carrier into engagement with said working head, and said externally directed teeth of said tool carrier are enabled to move out of engagement with said rows of internally directed teeth of said working head when said reversible ratchet wrench is rotated in an opposite direction, and contact is made between said tool carrier and said second circumferential surface section of said chamber when said externally directed teeth are disposed in driving contact with said rows of internally directed teeth of said working head, whereby said externally directed teeth of said tool carrier engage said rows of internally directed teeth of said internal surface of said chamber such that when said tool carrier selectively engages said internal surface of said chamber, said tool carrier is constrained against disengagement by torque applied in one direction, and said tool carrier disengages from said internal surface of said chamber responsive to torque applied in an opposite direction, further including means for limiting torque applied to said tool carrier, comprising a first resiliently deflectable member, one said row of internally directed teeth of said internal surface being disposed upon said resiliently deflectable member, said first resiliently deflectable member supporting one said row of internally directed teeth of said working head, said first resiliently deflectable member disposed to be able to move by deflection, into a first position assuring engagement of one said row of internally directed teeth of said working head with said externally directed teeth of said tool carrier, and into a second position disengaging one said row of internally directed teeth of said working head from said externally directed teeth of said tool carrier.

18. The reversible ratchet wrench according to claim 17, said means for limiting torque applied to said tool carrier further comprising a second resiliently deflectable member anchored to said chamber of said working head, said second resiliently deflectable member supporting the other said row of internally directed teeth of said working head, said second resiliently deflectable member disposed to be able to move by deflection into a first position assuring engagement of the other said row of internally directed teeth of said working head with said externally directed teeth of said tool carrier, and into a second position disengaging the other said row of internally directed teeth of said working head from said externally directed teeth of said tool carrier.

19. A ratchet mechanism having interchangeable working inserts, comprising:

a working head having a handle and having means defining a chamber therein, said chamber having an internal surface having a first portion including at least one internally directed tooth and a second portion of smooth surface, a third portion including at least one internally directed tooth and a fourth portion of smooth surface, said first portion separated from said third portion by said second portion at one side of said first portion and by said fourth portion at another side of said first portion, said chamber having a major diameter and a minor diameter, said diameters designating said respective portions, the at least one internally directed tooth in the first portion being opposed to the at least one internally directed tooth in the third portion, and a tool driver rotatably disposed within said chamber, said tool driver having a circular external surface including externally directed teeth interfittably cooperating with said at least one internally directed tooth of said working head, said tool driver further having means for engaging a working insert usable with said ratchet mechanism, said working head further having means for biasing said tool driver into engagement with said working head by urging said externally directed teeth of said tool driver into interfitting engagement of said at least one internally directed tooth of said working head when said handle is rotated in a first direction and out of engagement with said working head by urging said externally directed teeth of said tool driver away from interfitting engagement of said at least one internally directed tooth of said working head when said handle is rotated in a second direction opposite of said first direction, wherein said engagement and disengagement effects ratcheting in the first direction, the ratcheting mechanism being inverted for ratcheting in the second, opposite direction.

20. A reversible ratchet wrench for driving interchangeable tools, comprising:

a first working head having an externally projecting handle and a chamber formed within said first working head, said chamber having a concave, curved internal surface having a first circumferential surface section including:

a first row of internally directed teeth, a second, adjacent circumferential surface section of smooth surface, a third adjacent circumferential surface section including a second row of internally directed teeth, and a fourth circumferential surface section of smooth surface disposed between said first circumferential surface section and said third circumferential surface section, said internal surface having a major diameter dimension and a minor diameter dimension, said major and minor diameter dimensions designating said respective sections, a driven tool carrier rotatably disposed within said chamber, said tool carrier having a generally circular external surface having externally directed teeth interfittably cooperating with said first row and said second row of internally directed teeth of said working head as selected, said tool carrier further having tool engaging apparatus keyed to drivably engage a tool usable with said reversible ratchet wrench.

* * * * *